United States Patent [19]
Childers et al.

[11] Patent Number: 5,830,409
[45] Date of Patent: Nov. 3, 1998

[54] METHOD TO SHORTEN AERATION AFTER A STERILIZATION CYCLE

[75] Inventors: Robert W. Childers, New Port Richey, Fla.; Steven J. Edwards, Apex, N.C.; Donald R. Gagne, Placerville, Calif.; Cory J. Palmer, Clayton, N.C.

[73] Assignee: American Sterilizer Company, Mentor, Ohio

[21] Appl. No.: 582,731

[22] Filed: Jan. 4, 1996

[51] Int. Cl.$^6$ ........................................................ A61L 9/00
[52] U.S. Cl. ................................. 422/30; 422/1; 422/31; 422/33
[58] Field of Search .................................. 422/1, 30, 31, 422/33

[56] References Cited

U.S. PATENT DOCUMENTS

| | | |
|---|---|---|
| Re. 33,007 | 8/1989 | Bier . |
| 3,992,147 | 11/1976 | Christian . |
| 4,169,123 | 9/1979 | Moore . |
| 4,169,124 | 9/1979 | Forstrom . |
| 4,238,447 | 12/1980 | Wolff . |
| 4,241,010 | 12/1980 | Baran . |
| 4,321,232 | 3/1982 | Bithell . |
| 4,368,081 | 1/1983 | Hata . |
| 4,521,375 | 6/1985 | Houlsby . |
| 4,687,635 | 8/1987 | Kaehler . |
| 4,756,882 | 7/1988 | Jacobs . |
| 4,770,851 | 9/1988 | Joslyn . |
| 4,822,563 | 4/1989 | Joslyn ........................................ 422/31 |
| 4,909,999 | 3/1990 | Cummings . |
| 4,941,519 | 7/1990 | Sestak . |
| 4,944,919 | 7/1990 | Powell . |
| 5,068,087 | 11/1991 | Childers . |
| 5,118,471 | 6/1992 | Andersen . |
| 5,286,448 | 2/1994 | Childers . |
| 5,440,104 | 8/1995 | Koch . |
| 5,445,792 | 8/1995 | Rickloff . |

FOREIGN PATENT DOCUMENTS

| | | |
|---|---|---|
| 0 243 003 | 10/1987 | European Pat. Off. . |
| WO 8203774 | 11/1982 | WIPO . |
| WO 9411034 | 5/1994 | WIPO . |
| WO 95/05203 | 2/1995 | WIPO . |

OTHER PUBLICATIONS

Johnson, John W., et al., Nov. 1992. Vaporized Hydrogen Peroxide Sterilization of Freeze Dryers. Journal of Parenteral Science & Technology 46: 215–225.

Sterilization Technology, Robert F. Morrissey and G. Briggs Phillips, Ed. Van Nostrand Reinhold, New York. pp. 164–168, 402–420 No Date Available.

Rickloff, James R., Oct. 1988. The Development of Vapor Phase Hydrogen Peroxide as a Sterilization Technology. HIMA Sterilization in the 1990's Conference. Washington, DC. pp. 53–65.

Schneider, Philip M. Jan. 1994. Low–temperature sterilization alternatives in the 1900s. Tappi Journal 77(1): 115–119.

Graham, G.S., Rickloff, J.R. and Dalmasso, J.P., Feb. 1992. Sterilization of Isolators and Lyophilizers with Hydrogen Peroxide in the Vapor State. (citation unavailable). pp. 32–51.

AMSCO VHP™ DV1000 Technical Data, 15 pages. No Date Available.

Guideline for Industrial Ethylene Oxide Sterilization of Medical Devices Mar. 1988. Association for the Advancement of Medical Instrumentation, pp. 286–287, 290.

Charrier, Jean–Michel. 1990. Polymeric Materials and Processing. Plastics, Elastomers and Composites. Hanser Publishers, New York. pp. 364–365.

*Primary Examiner*—Krisanne Thornton
*Attorney, Agent, or Firm*—Fay, Sharpe, Beall, Fagan, Minnich & McKee

[57] ABSTRACT

Hot, saturated water vapor in the form of low-temperature subatmospheric steam is employed to shorten the aeration period after sterilization with a condensable, heat-labile chemical sterilant. The application of steam accelerates the rate of outgassing of sterilant residuals that are absorbed into, or adsorbed or condensed onto chamber or load materials. The method is particularly suitable for removing residuals from polymeric materials and/or materials that are poor heat conductors. Apparatus is provided to supply steam in situations where a utility steam supply is not available.

12 Claims, 5 Drawing Sheets

METHOD TO SHORTEN AERATION AFTER A STERILIZATION CYCLE

BACKGROUND

The effective and rapid elimination of sterilant residues in a chamber and/or a sterilized load or product after a sterilization cycle is a problem common to industrial, scientific and medical sterilization processes. Commonly used sterilant gasses, such as ethylene oxide and formaldehyde, are considered to be carcinogenic, and liquids and vapors, such as hydrogen peroxide and peracetic acid, can be corrosive. Therefore, residual sterilant entering the working environment could pose a potential health hazard to the sterilizer user; and residual sterilant remaining in a sterilized load could pose a potential health hazard to both user and/or hospital patient if there is physical contact with the material.

When goods are in storage after sterilization and aeration, they often tend to outgas slightly and if a room is full of outgassing goods, the residual vapors in the air can be significant. Frequently, it is necessary to quarantine sterilized products in a dedicated aeration cell or room to allow product outgassing. The addition of such a distinct aeration chamber necessarily adds expense to the overall sterilization unit and extra process steps which lengthen the sterilization cycle. In cases where regulations specify extremely low residue limits, it may be necessary to hold sterilized product for excessively long periods of time before it is available for sale and/or patient use.

Outgassing of residual sterilant can be a particular problem when chamber components (e.g. chamber walls and doors) or the sterilized products or loads are manufactured from certain types of materials. For example, ethylene oxide diffuses very slowly from "hard" polymers (e.g. acrylic and amide polymers), polyvinylchloride, kraft paper and glassine Hydrogen peroxide tends to be substantially absorbed by cellulosic materials and to a lesser degree by acrylic, polycarbonate, polypropylene/polyester and polyvinylchloride materials. Yet hydrogen peroxide is not substantially absorbed by, for example, polyethylene and polypropylene. The use of hydrogen peroxide or peracetic acid to decontaminate or sterilize chambers, such as freeze dryers which frequently have plastic (e.g. acrylic) doors or polymeric gaskets and/or valves, can necessitate prolonged periods of aeration after sterilization due to continuous outgassing of retained hydrogen peroxide vapor. Sterilizable products, such as nebulizers, dental appliances, catheters, syringes, tubing and food packages also may be manufactured of materials that tend to absorb hydrogen peroxide and require long periods of aeration after sterilization.

Sterilant residuals subject to outgassing may be in the form of sterilant that is absorbed into the load or chamber materials, adsorbed onto the surfaces of the load or chamber, or condensed in the load or on chamber surfaces. All three of these forms of residual sterilant are much more difficult to remove than free sterilant gas or vapor remaining in the chamber or interstices of the load at the end of the sterilization cycle. Traditionally, residual sterilant gasses, such as ethylene oxide, formaldehyde and hydrogen peroxide vapor, are removed by a lengthy period of aeration after sterilization has occurred. Aeration is typically accomplished by repeatedly evacuating the chamber and its contents and then backfilling with fresh air. This "pulsing" is often combined with a flow through of fresh air which further helps to flush out any residual gasses. However, outgassing of the absorbed and adsorbed residual sterilant from the product and chamber materials and surfaces, and/or evaporation of condensed sterilant, can continue to replenish the residual free gasses or vapors for hours during aeration. This is evidenced by the extended aerations (i.e. up to 24 hours or more) necessary at the end of ethylene oxide sterilization cycles.

Aeration after sterilization with hydrogen peroxide vapor or peracetic acid is usually not as prolonged as that for ethylene oxide because the initial sterilant concentration is typically lower. However, aeration after hydrogen peroxide sterilization may still consume more time than sterilization because the aeration method simply continues to remove the vapors as they are being constantly desorbed or outgassed. Aeration alone does not speed up outgassing or eliminate the residuals before they are outgassed.

Several methods other than aeration have been proposed to eliminate residual chemical sterilants. For example, subatmospheric superheated steam has been described as a method for removing trapped residual non-condensable gasses, such as ethylene oxide, from loads such as towels, sheets and tubing, that contain voids or spaces. The method relies on the condensation of the steam into the interstices of the load or on the chamber surfaces. The steam is then revaporized and carries away the non-condensable gas.

Solutions of anti-oxidants, reducing agents or enzymes which decompose hydrogen peroxide, have been applied to the surface of certain products, such as food packages or contact lenses, to remove sterilant residuals. However, such solutions are not suitable for eliminating free residual vapor in sterilization chambers, nor are they suitable for porous loads or loads that are overwrapped.

Another aeration method employs generation of a radio frequency (RF) plasma field around an item containing hydrogen peroxide residuals, to decompose the sterilant. However, RF is expensive to use and does not penetrate metals, like the wire cages frequently used to hold product in a sterilization chamber, the metal racks and shelves which support the load being sterilized, or the metal shelves and metal refrigeration coils of a freeze dryer.

Heating of the chamber walls with an electric blanket or steam jacket may effectively accelerate decomposition of heat-labile gasses, such as hydrogen peroxide, and hasten the aeration of the chamber itself. However, such heating would not significantly affect the aeration of objects contained in the chamber, since heating of the chamber walls would not necessarily provide efficient transfer of thermal energy to the objects. Other forms of energy, such as RF, microwaves and ultrasonics, also cannot transfer thermal energy quickly enough and evenly enough to uniformly accelerate the elimination of residual gasses. In addition, such energy sources cannot penetrate certain load materials, into dead legs or through metal shelving etc., and outgassing of sterilant residuals from inaccessible areas may continue even after aeration appears to be complete by measurement of free residuals in the chamber. Moreover, methods employing the above energy sources are limited to destroying the residuals when they are in the vapor form and do not affect residuals that may be condensed in the load or on the surfaces of the load and chamber. More importantly, sterilant residues absorbed into or adsorbed onto chamber or load materials that are poor heat conductors would be substantially unaffected by the application of heat.

Therefore, while several techniques may be contemplated for speeding up the aeration process, none perform adequately in providing uniform and substantially complete elimination of residuals, as would be required for optimum safety.

In view of the above considerations, there is a need for an enhanced aeration method that will effectively and quickly remove condensable sterilant residuals, such as residual hydrogen peroxide or peracetic acid, from a sterilization chamber and/or a sterilized load. Such a method should be particularly effective to remove absorbed and adsorbed sterilant residuals from chamber and/or load materials that are poor heat conductors, as well as those that are good heat conductors. Such a method should also be effective as applied to chambers and/or loads that include metal parts.

SUMMARY OF THE INVENTION

The present invention employs low-temperature, subatmospheric steam to shorten the period of aeration that accompanies sterilization with a condensable, heat-labile chemical sterilant, such as hydrogen peroxide or peracetic acid. The application of steam accelerates the rate of outgassing of sterilant residuals in the chamber and/or load, particularly from materials that have low thermal conductivity, and thus quickly removes residuals that previously were difficult to eliminate. The method is particularly suitable for a sterilization chamber (including a freeze dryer) and/or a load containing or comprising metal and/or polymers which, by their chemical nature, tend to absorb or adsorb a condensable sterilant, such as hydrogen peroxide vapor.

Apparatus is also provided to supply steam for the method of the invention in situations where a utility steam supply is not available.

In accordance with the present invention, hot, saturated water vapor, in the form of low-temperature steam, is introduced into a chamber which has been evacuated to remove substantially all free sterilant vapor. The temperature of the steam is controlled and maintained at a predetermined level so that condensation of the steam is substantially avoided and the steam remains in a vapor state. The steam-filled chamber is maintained at the predetermined temperature for a period of time sufficient to allow substantially all of the absorbed and adsorbed residual sterilant vapor to outgas. Following this time period, air is introduced into the chamber to dilute the steam and raise the pressure in the chamber to a higher subatmospheric level. The air introduction step is followed by re-evacuation of the chamber to remove the steam, free sterilant residuals and air mixture. The steps of the method may be repeated as often as necessary in order to rapidly and effectively reduce the sterilant residuals to a predetermined level. Following the final evacuation step, the chamber is returned to atmospheric pressure.

BRIEF DESCRIPTION OF THE DRAWINGS

The present invention can be better understood by reference to the drawings in which.

DETAILED DESCRIPTION OF THE INVENTION

Figure 1:
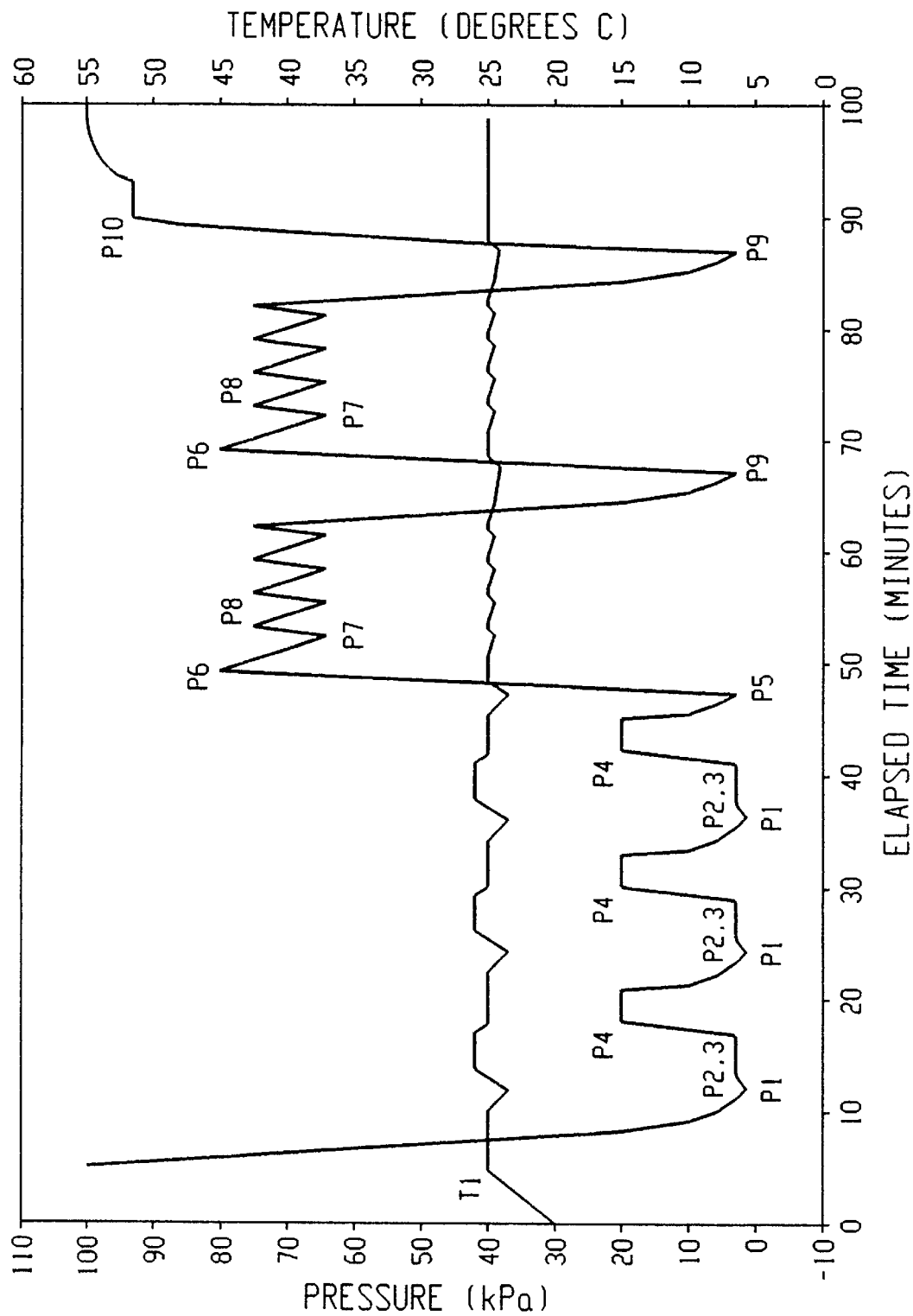
FIG. 1 illustrates an example of a prior art deep vacuum hydrogen peroxide vapor sterilization and aeration cycle.

The present invention employs hot, saturated water vapor in the form of low-temperature subatmospheric steam to reduce significantly the time required to aerate a sterilization chamber and/or sterilized load to a predetermined level of a residual condensable chemical sterilant. The invention is especially useful for chambers and/or loads manufactured from materials that, due to their chemical nature, tend to absorb and/or adsorb sterilant vapors, and materials that have low thermal conductivity. It was unexpectedly found that the interaction of the hot, saturated water vapor and the absorbed/adsorbed sterilant vapor molecules produces a more rapid than expected removal of sterilant residuals from materials having low thermal conductivity, as well as those having high thermal conductivity. The invention is also useful for loads that are heat-sensitive or heat-labile and necessitate low-temperature sterilization cycles.

It is contemplated that the method may be practiced with any condensable gas sterilant. Preferably, the invention may be practiced with hydrogen peroxide vapor or peracetic acid as the sterilant. The hydrogen peroxide vapor is preferably generated from a 30–35 percent (by weight) aqueous hydrogen peroxide solution.

The preferred apparatus of the invention provides a source of steam comprising a cartridge, containing a liquid comprising water, which may be used with, and is particularly suited to, hydrogen peroxide vapor sterilization systems employing a hydrogen peroxide vaporizer, such as those described in commonly owned U.S. Patents RE 33007 and 5,068,087, the disclosures of which are hereby incorporated by reference. The cartridge is fluidly connected to the vaporizer where liquid from the cartridge is controllably vaporized into steam, which then passes into the sterilization chamber. The apparatus allows the invention to be practiced in locations, such as medical or dental offices, where a utility steam supply is not available or where other access to sterile, distilled water is unavailable or inconvenient.

The invention may be practiced with any sterilization system or sterilization cycle that includes an aeration phase after the sterilization phase. Examples of such sterilization systems include cycles employing a sterilant gas or vapor in a deep vacuum, a sterilant gas or vapor including a flow-through of inert carrier gas, and combinations thereof. Preferably, the method of the invention is used after the sterilization phase of a cycle employing deep vacuum, and the chamber has been evacuated to substantially remove free (unabsorbed, unadsorbed and/or uncondensed) sterilant vapor residuals. The invention may be practiced in any sterilization chamber, including freeze dryers and isolation chambers, and including chambers having metal and/or polymeric parts, such as acrylic doors, polymeric gaskets and valves and/or polymeric or metal piping. The load to be sterilized may be any type of load that can be sterilized with a condensable sterilant. Such loads may contain or comprise polymeric and/or metal components and may be porous or non-porous loads. Typical of such loads would be "hard" goods, such as medical or dental instruments, including polymeric tubing, and "soft" goods, such as towels and sheets. The invention is particularly suited for aerating chambers or loads comprising polymeric materials which absorb or adsorb condensable sterilant vapors or gas, and for chambers or loads comprising materials that are poor heat conductors.

By the method of the present invention, low-temperature steam is introduced into a sterilization chamber that has been evacuated at the end of the sterilization phase. The method may or may not include an "air admit" prior to evacuation to facilitate substantial removal of free sterilant vapor and excess humidity from the chamber and/or load. As will be seen, prior removal of free vapor is optional and not essential to the method.

The temperature of the steam is predetermined and is selected to be low enough that any heat-labile objects in the chamber will not be damaged. Heat from the steam is quickly transferred uniformly to all parts of the chamber. The steam penetrates into deadleg piping, through Tyvek wraps, cloth wraps, etc. and warms up the entire chamber and its contents to a temperature of about 40° C.–60° C. and preferably to about 50° C. Any metal racks and shelves, as well as the chamber itself, will also be warmed to about 40° C.–60° C. and preferably about 50° C. The temperature of the steam is controlled and maintained at about 50° C. so that condensation of the steam is substantially avoided, and the steam remains in a vapor state. The heat transferred from the steam to the chamber and load produces a significant increase in the rate of decomposition of free residual sterilant vapor and vapor condensed in the chamber or load. For example, it is known that an increase in temperature from ambient to about 50° C. increases the decomposition rate of hydrogen peroxide, into oxygen and water, by nearly eight-fold. Therefore, free residual vapor and condensed vapor in the chamber and/or load may be substantially decomposed by heat due to the introduction of the steam. A portion of the sterilant vapor absorbed by and/or adsorbed to heat-conducting materials may also be degraded by heat, in situ.

Unexpectedly, however, it was discovered that the sub-atmospheric steam also produces a significant increase in the rate of outgassing of the vapor absorbed and/or adsorbed by chamber or product materials, especially those that are poor conductors of heat. As will be seen from the examples and preferred embodiment of the invention, which follow, when steam-enhanced aeration is used in connection with poor heat-conducting polymers such as acrylic, for example, the interaction between the hot, saturated water vapor and the hydrogen peroxide molecules produces a more rapid than expected removal of sterilant residuals from these materials. In the preferred embodiment, the invention is utilized after a deep vacuum hydrogen peroxide vapor sterilization cycle has been completed and aeration begins. Turning now to the drawing figures, examples will be utilized to describe the invention. Residual levels of hydrogen peroxide vapor were measured by Drager Tubes (BGI Incorporated, Waltham, Md., Part No. 8101041, concentration range 0.1–3 ppm).

A typical prior art deep vacuum hydrogen peroxide vapor sterilization cycle with an aeration phase that does not employ the steam-enhanced aeration cycle of the invention is illustrated, for comparison purposes, in FIG. 1. The illustrated cycle is performed in a deep vacuum stainless steel chamber at a temperature of about 25° C. However, the maintained temperature may range from ambient temperature up to about 60° C., depending on the nature of the chamber or the load for which the sterilization cycle is used. The cycle includes evacuating the sterilization chamber from atmospheric pressure to a subatmospheric pressure P1. Sterilant vapor is then injected into the chamber, raising the pressure slightly to P2,3 where a short hold period takes place. Air is then introduced to raise the pressure in the chamber slightly (to P4) and drive the sterilant vapor into areas which are difficult to access (e.g. deadleg piping). The periods of evacuation, sterilant injection and air introduction, constituting a sterilization pulse, are then repeated a predetermined number of times until the chamber and/or load are decontaminated or sterilized. The final evacuation (to pressure P5) is followed by a predetermined number of aeration pulses. The aeration pulses comprise introduction of sterile, filtered air to raise the pressure in the chamber to a pressure P6 slightly below atmospheric. A series of alternating shallow evacuations (to pressure P7) and inlet of air (to pressure P8), followed by a deep evacuation (to pressure P9) complete one aeration pulse. The number of aeration pulses employed depends on the level of residual hydrogen peroxide vapor in the chamber after the sterilization phase and the desired reduction in this level. For hydrogen peroxide vapor, the desired residual level in the chamber after aeration is less than about 1 ppm, and more preferably about 0.1 ppm. Following sufficient aeration, the chamber is returned to atmospheric pressure.

Typical aeration times for the prior art cycle illustrated in FIG. 1, when steam enhancement is not employed, are shown in the following examples. A stainless steel freeze dryer and its associated metal shelving and piping were exposed to 1400 ppm of hydrogen peroxide vapor sterilant during four sterilant exposure pulses of approximately 12 minutes each. Aeration consisted of multiple pulses, each of which was comprised of an evacuation to 10 Torr with air being admitted to raise chamber pressure to 650 Torr. The results for this aeration are as follows:

| Number of Aeration Pulses | Residual Hydrogen Peroxide Level | Elapsed Time |
| --- | --- | --- |
| 20 | 3 ppm | 2:31:00 |
| 30 | 1.5 ppm | 3:46:00 |

As can be seen, this aeration method required an inordinately long period of time and nevertheless resulted in unacceptably high levels of residuals.

A similar cycle in which steam was not used was also found to not provide adequate results. This sterilization cycle differed from the previous example only in that the aeration pulses comprised an evacuation to 1 Torr. The results for this aeration are as follows:

| Number of Aeration Pulses | Residual Hydrogen Peroxide Level | Elapsed Time |
| --- | --- | --- |
| 20 | 0.1 ppm | 3:13:00 |
| 30 | <0.1 ppm | 4:58:00 |

With this method, the residual levels were acceptable, but the interval required for aeration was still inordinately long.

The aeration phase can be as much as twice as long as the sterilization phase. Aeration of flexible walled and/or rigid walled isolators after hydrogen peroxide vapor sterilization, for example, may require up to 24 hours of aeration to reduce residual hydrogen peroxide levels to 0.1 ppm, depending on the materials of construction.

Figure 2:
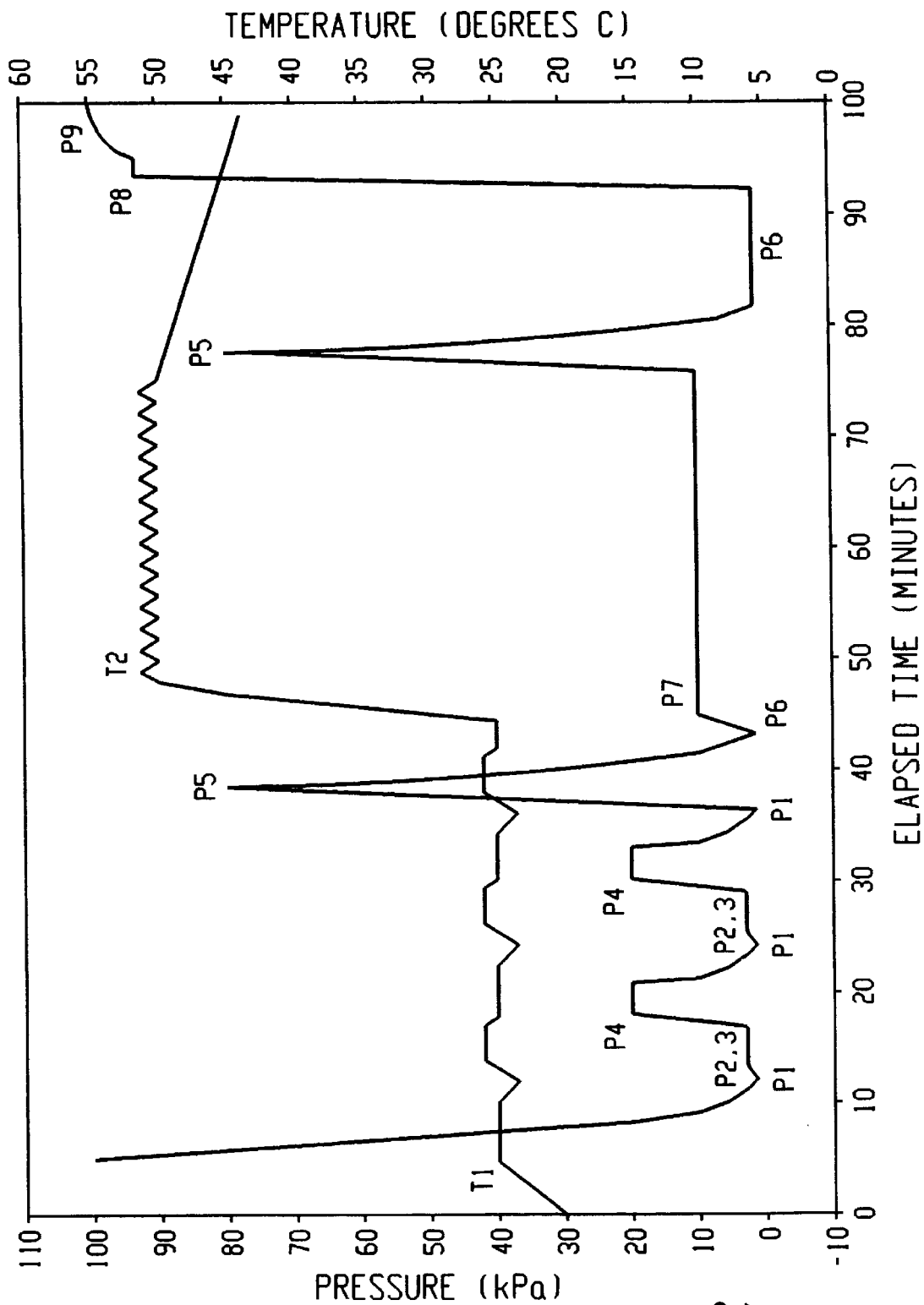
FIG. 2 illustrates a deep vacuum hydrogen peroxide vapor sterilization and aeration cycle of the invention where low-temperature subatmospheric steam is employed during the aeration phase.

The steam-enhanced aeration method of the present invention is illustrated schematically in FIG. 2, employing a deep vacuum hydrogen peroxide vapor sterilization system similar to that of FIG. 1. In the example, a stainless steel freeze dryer and associated metal shelving and piping are exposed to 1400 ppm of hydrogen peroxide vapor sterilant during sterilant exposure pulses of approximately 12 minutes each. The temperature of the chamber is maintained substantially at about 25 ° C. The final sterilization pulse ends with an evacuation step, followed by the introduction of sterile, filtered air to raise the pressure to a subatmospheric pressure P5, which is preferably at least ten times greater than the evacuation pressure P1 and which may be just slightly below atmospheric pressure. Preferably, P5 is about 80 KPa (608 Torr) and P1 is about 1.3 KPa (10 Torr). Following the air introduction, the chamber is re-evacuated to pressure P6, which is less than about 1.3 KPa (10 Torr), and preferably about 0.13 KPa (1 Torr). The step of air introduction and chamber re-evacuation prior to the introduction of steam into the chamber is preferable, but optional, to the method of the invention. The air introduction step serves to reduce humidity in the chamber which may have built up during the sterilization phase and helps to prevent undesirable condensation of the hydrogen peroxide vapor and/or steam that might occur when steam is subsequently introduced into the chamber. This step is preferable because condensed hydrogen peroxide or hydrogen peroxide dissolved in condensed steam (i.e. water) is more difficult to eliminate than free hydrogen peroxide vapor. Further, non-condensation of the steam is important in order to avoid creating "wet loads" which can be easily compromised if later exposed to microbial contamination.

The deep evacuation of the chamber before the steam-enhanced aeration of the invention removes free sterilant residuals and any air which, if present in appreciable amounts, might prevent steam from penetrating adequately into areas which may be difficult to access, such as deadleg piping and/or the interstices of a load. The maintenance of a deep vacuum during the presence of the steam in the chamber is also preferable in order to remove any moisture that might result from condensation of the steam as it transfers thermal energy to the chamber walls, shelves, and/or load, etc.

In the preferred embodiment of the invention, the steam-enhanced aeration begins after the sterilization phase, when the chamber has been evacuated to about 0.13 KPa (1 Torr). Preferably, residual free hydrogen peroxide vapor and excess humidity in the chamber have been substantially removed by a preliminary air introduction and evacuation step, as described above. Steam is then admitted until the temperature in the chamber reaches about 50° C. The introduction of the steam raises the pressure in the chamber slightly, to pressure P7, about 10 KPa (76 Torr). The chamber temperature is then maintained at about 50° C. for about 30 minutes by intermittent re-introduction of steam as needed. The temperature of the steam is controlled and maintained so that condensation of the steam in the chamber and/or load is substantially avoided, and the steam remains in a vapor state. During this time period, the subatmospheric pressure in the chamber may vary somewhat due to the repeated steam introductions.

After the steam-exposure phase, air is admitted into the steam-filled chamber until the chamber pressure again reaches P5, about 80 KPa (608 Torr) in order to dilute humidity in the chamber and prevent undesirable condensation of residual hydrogen peroxide vapor and/or steam prior to evacuation. The chamber is then evacuated to pressure P6, which is less than about 10 KPa (76 Torr), and preferably about 0.13 KPa (1 Torr) in order to remove residual steam, air and hydrogen peroxide vapor. After a hold time of approximately 10 minutes, the chamber may either be returned to atmospheric pressure, or the aeration pulses, each comprising the above-described steps of steam introduction, air admit and evacuation, may be repeated a predetermined number of times to render the chamber safe for unloading. The number of aeration pulses employed depends on the level of residual hydrogen peroxide vapor in the chamber after the sterilization phase and the desired reduction in this level. For hydrogen peroxide vapor, the desired residual level in the chamber after aeration is less than about 1 ppm, and more preferably about 0.1 ppm.

A sterilization and aeration cycle utilizing the preferred method of the invention was performed in the stainless steel freeze dryer with associated metal shelves and piping. It was found that, after a single steam-enhanced aeration pulse, the hydrogen peroxide vapor residuals within the chamber were below 0.1 ppm. The chamber was then allowed to sit unopened for approximately one hour, to allow any remaining absorbed or adsorbed vapor residuals to desorb, after which the level of residuals in the chamber was again measured. The residuals were still below 0.1 ppm, indicating that substantially all residual absorbed and adsorbed hydrogen peroxide had been removed during the steam-enhanced aeration. A complete aeration of the sterilization chamber had been accomplished with a single aeration pulse in less than one hour.

Thus, it is clear that the use of low-temperature, subatmospheric steam significantly shortens the aeration phase of a hydrogen peroxide vapor sterilization cycle.

Figure 3:
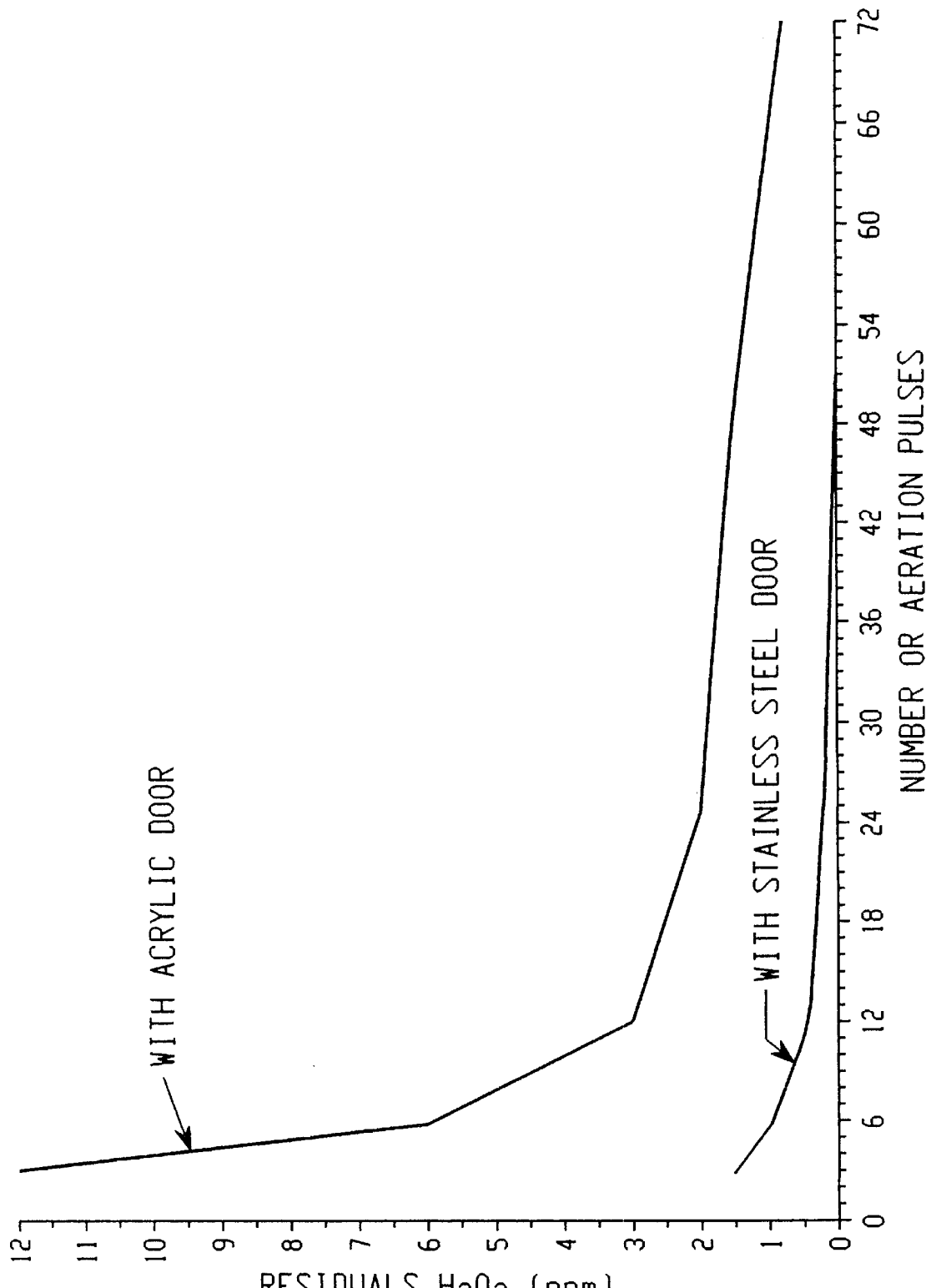
FIG. 3 illustrates a comparison of hydrogen peroxide vapor residuals in a freeze dryer with a stainless steel door or an acrylic door, during aeration pulses of the prior art.

The difference in the aeration characteristics of a material, such as acrylic, which absorbs hydrogen peroxide vapor, and stainless steel, which substantially does not, is illustrated in FIG. 3. A stainless steel freeze dryer with a stainless steel door gasket is shown to be aerated to about 0.1 ppm hydrogen peroxide vapor in about two hours during approximately 24 aeration pulses using the alternating evacuations and air admissions of the prior art. In contrast, a stainless steel freeze dryer with an acrylic door gasket requires more than three times as many pulses (more than 6 hours) to achieve residual hydrogen peroxide vapor levels of less than 1 ppm and would require still a longer period of time to reach 0.1 ppm.

Tests were conducted to determine if elevated temperature alone, without the use of steam, would reduce the level of hydrogen peroxide residuals during aeration. Two stainless steel freeze dryers, one having a stainless steel door gasket and the other having an acrylic door gasket, were subjected to identical sterilization cycles similar to that illustrated in FIG. 1. However, during aeration, hot dry air was flowed into and through the chamber to heat the door and the shelves of the freeze dryers to approximately 24 ° C., or 40° C., or 65° C., respectively. Residual hydrogen peroxide levels were measured after an identical number of aeration pulses. The results of these tests showed that increased temperature alone had a negligible effect on the number of aeration pulses required to reduce the residual vapor to acceptable levels (data not shown).

Figure 4:
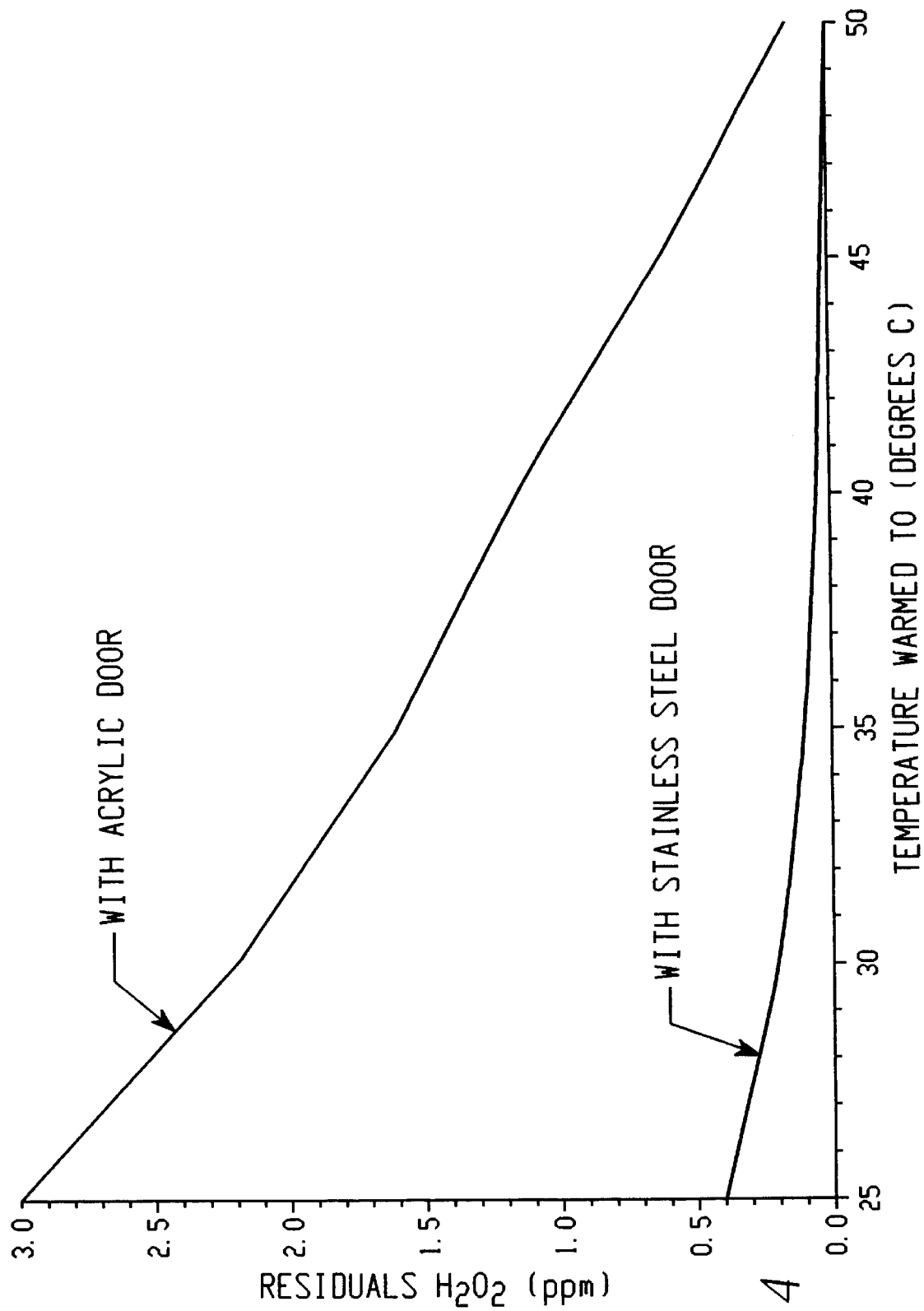
FIG. 4 illustrates the effect of the temperature of subatmospheric steam on hydrogen peroxide vapor residuals in a freeze dryer with a stainless steel door or an acrylic door during aeration employing the present invention.

When hot subatmospheric, saturated water vapor was used during only one aeration pulse, however, the results were striking. As illustrated in FIG. 4, a single aeration pulse employing subatmospheric steam at 50° C. reduced the residual hydrogen peroxide vapor level in a stainless steel freeze dryer with an acrylic door gasket to 0.15 ppm without requiring any additional time, or any additional aeration pulses. In this test, single aeration pulses were carried out using subatmospheric steam at pre-selected temperatures ranging from 25° C. to 50° C. As a result, hydrogen peroxide vapor residuals in the stainless steel freeze dryer with an acrylic door decreased dramatically as the temperature of the water vapor was increased from 25° C. to 50° C. In addition, the use of subatmospheric, saturated water vapor, even at the lower sterilization temperature of 25° C., reduced the residual level of hydrogen peroxide found in the freeze dryer with the acrylic door gasket to 3 ppm, which is comparable to the level found after at least 12 aeration pulses in the same freeze dryer without the use of steam during aeration (see FIG. 3). Steam does not penetrate plastics, such as acrylic. Presumably, the 25° C. saturated water vapor facilitated the removal of a thin film of hydrogen peroxide adsorbed onto the surfaces within the freeze dryer. However, water vapor at 25° C. did not appear to increase the rate of desorption of absorbed hydrogen peroxide vapor.

As the temperature of the saturated water vapor increased from 25° C. through 50° C., the rate of desorption of the hydrogen peroxide absorbed by the acrylic door gasket increased dramatically, as evidenced by the striking reduction of residual vapors in the chamber. The demonstrated increased rate of desorption may be due partially to an elevation of the temperature of the acrylic, combined with the presence of the saturated water vapor which substantially prevents outgassed vapors from adsorbing onto surfaces within the freeze dryer. However, the effect of the increased temperature on the acrylic door is believed to be substantially insignificant since acrylic heats up very slowly because of its relatively poor heat conductivity, and because of the demonstrated negligible effect of elevated temperature alone on desorption, as described above. Instead, the dramatic increase in the rate of desorption of absorbed hydrogen peroxide vapor in the acrylic may illustrate a synergistic interaction between the hot, saturated water vapor and the hydrogen peroxide molecules.

FIG. 4 also illustrates that residual adsorbed and/or condensed vapors were more readily removed from the surface of the stainless steel door as the temperature of the steam was increased. Stainless steel does not absorb hydrogen peroxide, is a good heat-conducting material, and is not penetrated by steam. Therefore, there also appears to be a direct temperature-related elimination of hydrogen peroxide adsorbed and/or condensed on heat-conducting materials, in the presence of saturated water vapor, that is not observed when dry heat alone is used.

In summary, the low-temperature, subatmospheric steam-enhanced aeration method of the present invention significantly reduces the aeration time that accompanies sterilization with a condensable sterilant, such as hydrogen peroxide vapor. In addition to increasing the rate of decomposition of free vapor, the hot, saturated water vapor accelerates the rate of desorption of absorbed vapor from materials, such as acrylic, that are poor heat conductors. The combination of saturated water vapor and heat also significantly increases the rate of decomposition of residual sterilant adsorbed or condensed on the surfaces of heat-conducting materials. The significant reduction in aeration time permits a load to be aerated within the vessel where sterilization occurred, thus eliminating the necessity of a separate aerator with its associated costs. Also eliminated is the need to transfer an outgassing load from the sterilizer to the aerator, thus greatly reducing the potential for exposing operating personnel to residual sterilant. The invention also reduces the possibility of false residual readings after aeration. Since residuals in the materials which make up the chamber, shelves and load are substantially eliminated, the potential for a gradual buildup in residuals due to outgassing after a loaded chamber has been allowed to sit before being unloaded is greatly reduced. The invention also substantially eliminates the danger that goods in storage after sterilization and aeration will continue to outgas into the environment.

The present method adds little if anything to the cost to the construction of a sterilizer. Elaborate elements such as a pressure vessel are not required since the steam is introduced and maintained at a low subatmospheric pressure. Thus, many existing sterilizer designs can be adapted for use with the present invention simply by the addition of a steam supply.

A "utility" steam supply from a steam line, with associated piping and valving, may be used with the method of the present invention. However, the use of utility steam has certain drawbacks and is not the preferred steam supply. The temperature of utility steam is typically much warmer than 50° C. and, when introduced into to a deep vacuum chamber held at near room temperature, unwanted superheated steam would be introduced. In addition, over time, an undesirable hot spot may result in the chamber at the point of attachment of the utility steam line.

A preferred system for delivering steam in the method of the invention utilizes a vaporizer to provide steam and to control the temperature and concentration of the steam delivered to the chamber. The vaporizer employed in the system may be added to an existing sterilization apparatus or may employ an existing vaporizer, such as that included in certain hydrogen peroxide vapor sterilization systems known in the art. The vaporizer is fluidly connected to a portable reservoir, such as a cartridge, containing a liquid comprising water. The vaporizer is also fluidly connected to a sterilization chamber. When a vacuum exists in the chamber, the liquid is drawn from the reservoir through an open valve into the vaporizer, and thence into the chamber. In the system of the present invention, steam may be generated from any liquid containing water, for example, alcohol, such as isopropanol. However the generation of steam from sterile, distilled water is preferred in the method of the invention.

Figure 5:
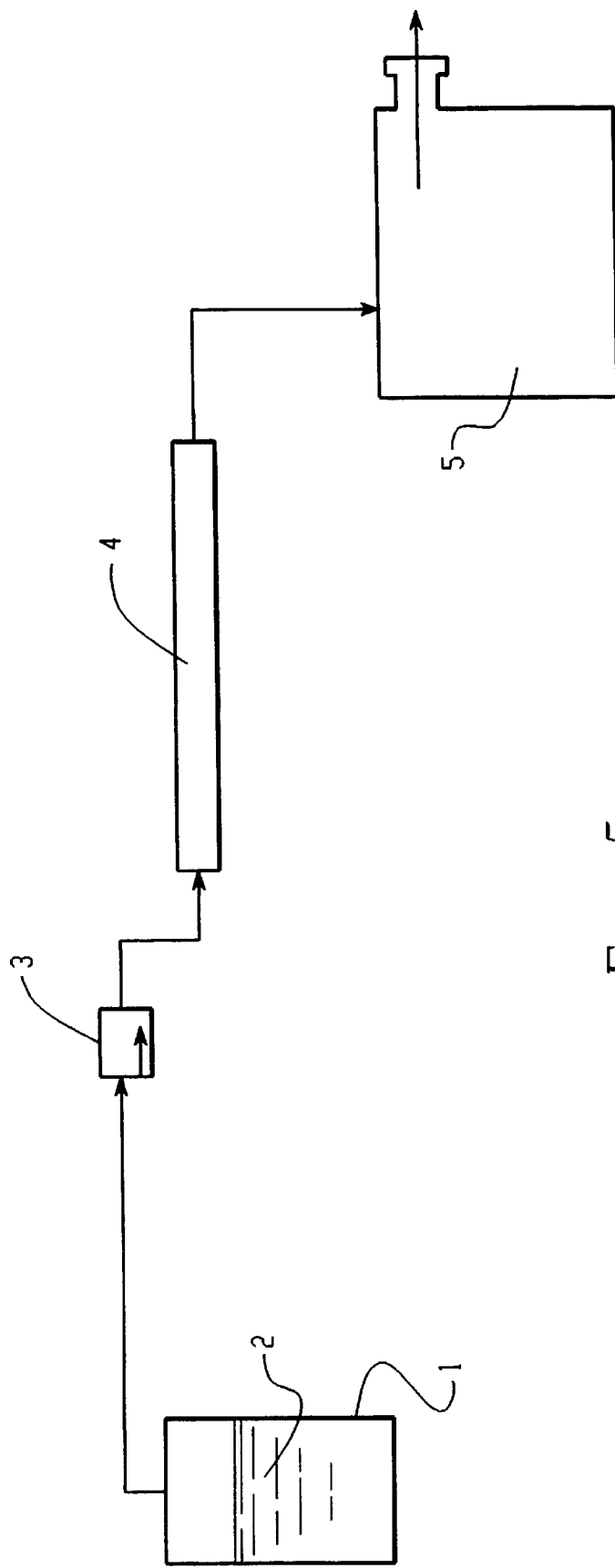
FIG. 5 is a schematic illustration of an apparatus to supply steam in the method of the invention.

As schematically illustrated in FIG. 5, a portable cartridge (1) containing sterile distilled water (2) is fluidly connected through a two-way valve (3) and optional filter (4) to a pre-heated vaporizer (5). The vaporizer (5) is also fluidly connected to a sterilization chamber (not shown). During the aeration phase of the sterilization cycle of the invention, the chamber is under vacuum, thus providing the force needed to draw the distilled water or other liquid from the cartridge into the vaporizer when the two-way valve is open. Once the distilled water comes in contact with the hot surfaces of the vaporizer, it is converted into steam. The two-way valve is pulsed, allowing distilled water into the vaporizer, and steam into the chamber until a predetermined chamber temperature is achieved. The chamber temperature may then be maintained by controlling the amount of liquid reaching the vaporizer and thus the amount of steam entering the chamber. Thus, condensation of the steam in the chamber may be avoided.

The supply of sterile water is preferably located so that it is easily accessible to and can easily be refilled by the user. In a sterilization system employing hydrogen peroxide, as described above, the cartridge containing hydrogen peroxide used for the sterilization phase may be removed and replaced by a cartridge of distilled water for use in the aeration phase of the cycle.

This system provides a functionally safe and simple means of introducing subatmospheric steam into the chamber and may also be software-controlled. By the apparatus, the means of introducing the sub-atmospheric steam is self-contained within the sterilizer, and eliminates the need for utility steam to be attached to the unit. The use of the cartridge, fluidly connected to the vaporizer unit, allows the invention to be practiced in locations, such as medical or dental offices, where a utility steam supply is not available or where access to sterile, distilled water is unavailable or inconvenient.

While the invention has been described herein with reference to the preferred embodiments, it is to be understood that it is not intended to limit the invention to the specific forms disclosed. On the contrary, it is intended to cover all modifications and alternative forms falling within the spirit and scope of the invention.

We claim:

1. In a method of sterilization at subatmospheric pressure with a sterilant vapor in a sterilization chamber, at least one of an article in the sterilization chamber and components of the sterilization chamber absorbing sterilant residuals during the sterilization, the improvement comprising:

(a) introducing low temperature steam in vapor form into the sterilization chamber raising the pressure therein to a subatmospheric steam phase pressure and raising temperature in the sterilization chamber to a steam phase temperature;

(b) maintaining the steam in vapor form in the sterilization chamber as the absorbed sterilant residuals are released in vapor form into the steam.

2. In the method as set forth in claim 1, the improvement further comprising:

(c) after step (b), admitting air into the sterilization chamber raising the pressure in the sterilization to a subatmospheric air phase pressure greater than the subatmospheric steam phase pressure.

3. In the method as set forth in claim 2, the improvement further comprising:

(d) reducing the subatmospheric pressure in the sterilization chamber to evacuate air, residual sterilant vapor, and steam.

4. In the method as set forth in claim 3, the improvement further comprising:

repeating at least steps (a), (b), (c) and (d) until a level of the residual sterilant is less than 1 ppm.

5. In the method as set forth in claim 3, the improvement further comprising:

in step (d), reducing the pressure in the sterilization chamber at least to 1 Torr.

6. In the method as set forth in claim 1, the improvement further comprising:

the sterilant vapor being heat-labile.

7. In the method as set forth in claim 6, the improvement further comprising:

the sterilant being selected from the group consisting of hydrogen peroxide vapor, peracetic acid vapor, and mixtures thereof.

8. In the method as set forth in claim 1, the improvement further comprising:

generating the steam from one of (i) distilled water and (ii) a mixture of distilled water and alcohol.

9. In the method as set forth in claim 1, the improvement further comprising:

the steam phase temperature being in the range of 40°–65° C.

10. A method to shorten the time for removing residual peracetic acid from an evacuated chamber, said method comprising:

(i) admitting steam into said chamber containing residual peracetic acid to raise the pressure in said chamber to a first subatmospheric pressure and to raise the temperature in said chamber to a predetermined temperature, while maintaining the steam substantially in vapor form;

(ii) maintaining said chamber at said predetermined temperature for a period of time sufficient to reduce the level of residual peracetic acid in said chamber;

(iii) admitting air into the steam-filled chamber to raise the pressure in said chamber to a second subatmospheric level;

(iv) evacuating said chamber to remove the air, residual peracetic acid vapor, and steam; and (v) repeating steps (i) through (iv) until an acceptable level of residual peracetic acid in said chamber is achieved.

11. A method to shorten the time of removing residual hydrogen peroxide from an evacuated chamber, said method comprising the steps of:

(i) introducing air into said chamber at an evacuated pressure and containing residual hydrogen peroxide to raise the pressure in said chamber to a subatmospheric level at least ten times greater than said evacuated pressure;

(ii) evacuating air introduced from step (i), from said chamber;

(iii) admitting steam into said chamber to raise the pressure in said chamber to a first subatmospheric pressure and to raise the temperature in said chamber to a predetermined temperature, while maintaining the steam substantially in vapor form;

(iv) maintaining said chamber at said predetermined temperature for a period of time sufficient to reduce the level of residual hydrogen peroxide in said chamber;

(v) admitting air into said chamber to raise the pressure in said chamber to a second subatmospheric level;

(vi) evacuating said chamber to remove substantially all air, residual hydrogen peroxide, and steam; and (vii) repeating steps (i) through (vi) until an acceptable level of residual hydrogen peroxide in said chamber is achieved.

12. A method to shorten the time for removing residual hydrogen peroxide vapor from items in a chamber, said method comprising:

(i) evacuating said chamber containing residual hydrogen peroxide vapor to a pressure of about 1 torr;

(ii) admitting steam into said chamber to raise the pressure in said chamber to a first subatmospheric pressure and to raise the temperature in said chamber to a predetermined temperature, while maintaining the steam substantially in vapor form;

(iii) maintaining said chamber at said predetermined temperature for a period of time sufficient to reduce the level of residual hydrogen peroxide vapor in said chamber;

(iv) admitting air into the steam-filled chamber to raise the pressure in said chamber to a second subatmospheric level;

(v) evacuating said chamber to remove the air, residual hydrogen peroxide vapor, and steam; and (vi) admitting air into the chamber, raising the pressure in said chamber to atmospheric, and removing the articles.

* * * * *